US00PP28776P2

(12) United States Plant Patent
Kamerman

(10) Patent No.: US PP28,776 P2
(45) Date of Patent: Dec. 19, 2017

(54) ***CLUSIA* PLANT NAME 'LICLUS01'**

(50) Latin Name: ***Clusia rosea* (L.).**
Varietal Denomination: LICLUS01

(71) Applicant: Handelsonderneming Licro, Uithoorn (NL)

(72) Inventor: Johan Albert Kamerman, Uithoorn (NL)

(73) Assignee: Handelsonderneming Licro, Uithoorn (NL)

( * ) Notice: Subject to any disclaimer, the term of this patent is extended or adjusted under 35 U.S.C. 154(b) by 61 days.

(21) Appl. No.: 14/999,668

(22) Filed: Jun. 10, 2016

(51) Int. Cl.
*A01H 5/12* (2006.01)
*A01H 5/04* (2006.01)

(52) U.S. Cl.
USPC ..... Plt./226
CPC ..... *A01H 5/12* (2013.01); *A01H 5/04* (2013.01)

(58) Field of Classification Search
None
See application file for complete search history.

*Primary Examiner* — Anne M Grunberg
(74) *Attorney, Agent, or Firm* — Samuel R. McCoy, Jr.

(57) ABSTRACT

A new and distinct *Clusia rosea* cultivar named 'LICLUS01' which is characterized by a broad and upright growth habit, ovate plant shape, very free branching, small dark green leaves that are very narrowly margined yellow-green, and the stability of these characteristics from generation to generation.

3 Drawing Sheets

Latin name of the genus and species: The Latin name of the genus and species of the novel variety disclosed herein is *Clusia rosea* (L.).

Variety denomination: The inventive variety of *Clusia rosea* disclosed herein has been given the variety denomination 'LICLUS01'.

BACKGROUND OF THE INVENTION

Parentage: 'LICLUS01' is the result of a spontaneous whole-plant mutation of *Clusia rosea* 'Princess' (not patented in the United States; Community Plant Variety Office Grant No. EU8456) which was discovered at the inventor's commercial greenhouse in Uithoorn, the Netherlands in January of 2015 and was ultimately selected for commercialization due to its freely branching habit and small, dark green leaves.

Asexual Reproduction: Asexual reproduction was initiated in July of 2015, by way of meristematic tissue culture, in Uithoorn, the Netherlands. Through two subsequent generations, the unique features of this cultivar have proven to be stable and true to type.

SUMMARY OF THE INVENTION

The cultivar 'LICLUS01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LICLUS01'. These characteristics in combination distinguish 'LICLUS01' as a new and distinct *Clusia rosea* cultivar:

1. 'LICLUS01' is a very freely branching plant; and
2. 'LICLUS01' exhibits a more a upright stem attitude; and 3. 'LICLUS01' exhibits dark green leaves that are very narrowly margined yellow-green; and
4. 'LICLUS01' exhibits small leaves.

BOTANICAL DESCRIPTION OF THE PLANT

Figure 1:
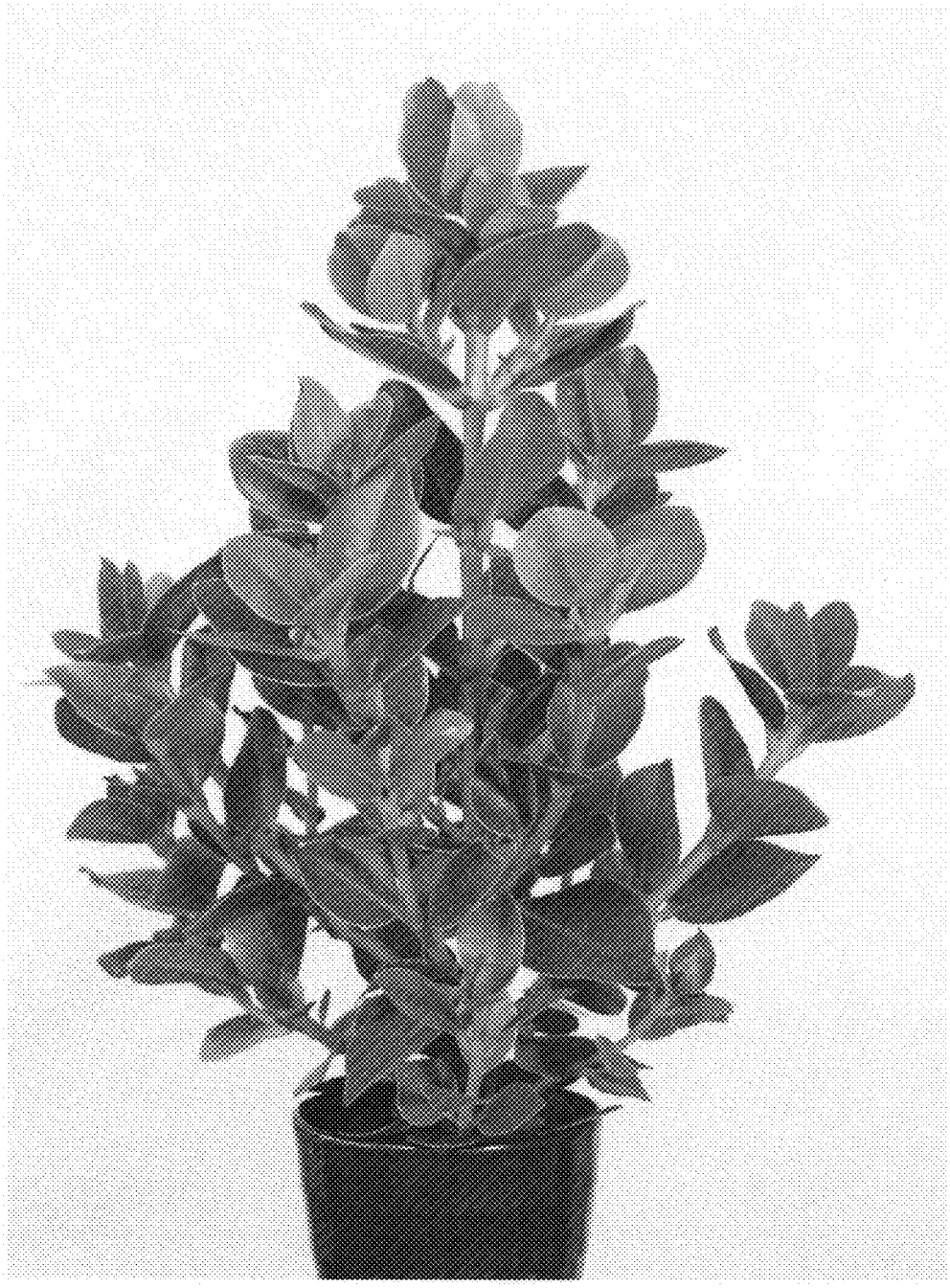
FIG. 1 illustrates, as nearly true as it is reasonably possible to make the same in color photographs of this type, an exemplary plant of 'LICLUS01' grown in a commercial greenhouse in Uithoorn, the Netherlands. This plant is approximately 6 months old, shown planted in a 12 cm nursery container.
Figure 2:
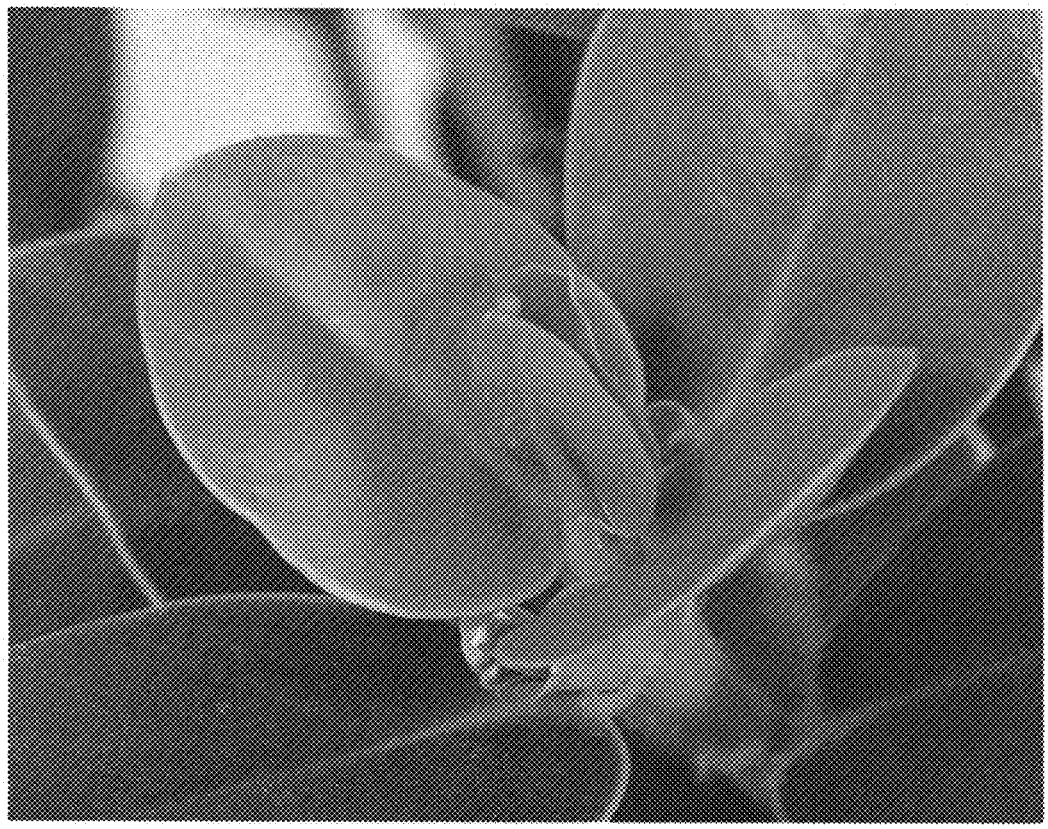
FIG. 2 illustrates, as nearly true as it is reasonably possible to make the same in color photographs of this type, the typical juvenile foliage habit of 'LICLUS01'.
Figure 3:
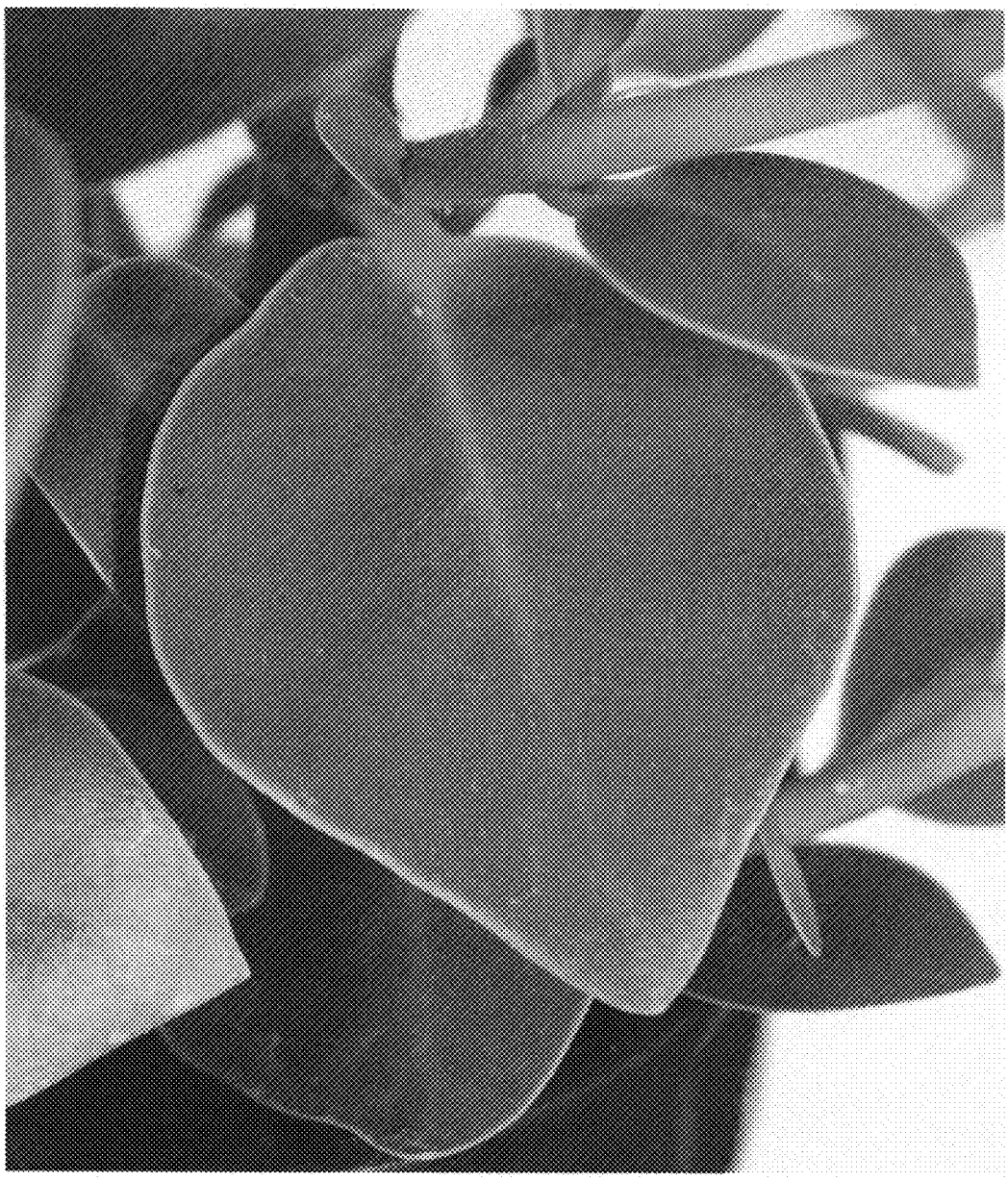
FIG. 3 illustrates, as nearly true as it is reasonably possible to make the same in color photographs of this type, the typical mature foliage habit of 'LICLUS01'.

The following observations and measurements made in April of 2016 describe averages from a sample set of six specimens of 6 month old 'LICLUS01' plants grown in 12 cm nursery containers at a commercial greenhouse in Uithoorn, the Netherlands. Plants were produced without the use of pest or disease control measures, and also without applying any fertilizer. Plants were grown under indirect sunlight and no photoperiodic treatments or artificial light was given to the plants. Irrigation was provided by way of flood benches.

Those skilled in the art will appreciate that certain characteristics will vary with older or, conversely, with younger plants. 'LICLUS01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LICLUS01' and a comparison with the parent and closest known comparator, *Clusia rosea* 'Princess', is provided below.

Plant description:

*Growth habit*.—Broad, upright growth habit.

*Plant shape*.—Ovate.

*Height from soil level to top of foliar plane*.—47.8 cm, on average.

*Plant diameter*.—Average of 36.8 cm.

*Growth rate*.—Moderate.

*Plant vigor*.—Moderate.

*Propagation*.—Type — Meristematic tissue culture. Time to initiate roots — Approximately 40 days at 21 degrees Celsius. Crop time — No less than 6 months, depending on the size of the container.

*Disease and pest resistance or susceptibility*.—Similar to other *Clusia* varieties.

*Environmental tolerances*.—Adapt to, at least, USDA Zones 10 to 13 and temperatures as high as 40 degrees Celsius; moderate tolerance to wind and rain.

Root system:

*General description*.—Small, fleshy, free-branching roots.

Stems:

*Branching habit*.—Basal branching, with one primary stem and eighteen lateral branches, on average; freely branching. All stems and branches produce a green-white (no corresponding RHS color) milky substance when damaged.

*Dimensions*.—Primary stem varies with age; oldest lateral branch is 11.8 cm long and 0.7 cm in diameter with an internode length of 3.5 cm, on average.

*Texture and luster*.—Glabrous and moderately glossy.

*Aspect*.—60 degrees from vertical.

*Strength*.—Strong.

*Color, juvenile*.—Yellow-green, RHS 144B.

*Color, mature*.—Yellow-green, RHS 144A, and aging to greyed-brown, RHS 199D.

*Color at internodes*.—Yellow-green, RHS 144A.

Foliage:

*Compound or simple*.—Simple.

*Arrangement*.—Opposite.

*Attachment*.—Petiolate.

*Quantity*.—Numerous; approximately 8 leaves per lateral branch.

*Shape*.—Broad ovate to broad elliptical.

*Dimensions*.—7.7 cm long by 6.1 cm wide, on average.

*Aspect*.—Flat; midrib is very slightly carinate.

*Apex*.—Broad, bluntly acute.

*Base*.—Obtuse to very short attenuate.

*Margin*.—Entire.

*Pubescence, texture and luster of adaxial surface*.—Glabrous, leathery, and moderately glossy to glossy.

*Pubescence, texture and luster of abaxial surface*.—Glabrous, leathery, and moderately glossy.

*Color*.—Juvenile foliage, adaxial surface — Yellow-green, RHS 144A, and very narrowly margined greyed-red, RHS 181A to 181B. Juvenile foliage, abaxial surface — Green, RHS 143C, and very narrowly margined greyed-red, RHS 181A to 181B. Mature foliage, adaxial surface — Green, RHS NN137A to NN137B, and very narrowly margined yellow-green, RHS 150D. Mature foliage, abaxial surface — Yellow-green, RHS 146B, and very narrowly margined yellow-green, RHS 150D.

*Venation*.—Venation pattern — Pinnate. Color, mature adaxial surface — Yellow-green, RHS 144A. Color, mature abaxial surface — Yellow-green, RHS 145B to 145C.

*Petiole*.—Length — 0.9 cm, on average. Cross-section — Flattened. Average diameter — Horizontal width of 0.7 cm and vertical width of 0.5 cm. Texture, pubescence and luster — Smooth, glabrous, and slightly to moderately glossy. Strength — Strong. Color, adaxial surface — Yellow-green, RHS 146C. Color, abaxial surface — Yellow-green, RHS 145A to 145B.

Inflorescence: No flowering has been observed to date.

Flower bud: No flowering has been observed to date.

Flower: No flowering has been observed to date.

Reproductive organs: No flowering has been observed to date.

Fruit and seed: No flowering has been observed to date.

COMPARISONS WITH THE PARENT PLANT AND CLOSEST KNOWN COMPARATOR

Plants of the new cultivar 'LICLUS01' differ from the parent *Clusia rosea* 'Princess', which is also the closest known comparator, in several physical characteristics which are compared in Chart 1.

CHART 1

| Characteristic | 'LICLUS01' | 'Princess' |
|---|---|---|
| Branching. | Very freely branching, with lateral branches. | Moderately branching, with lateral branches. |
| Leaf aspect. | 60 degrees to vertical. | 55 degrees to vertical. |
| Average leaf dimensions. | 7.7 cm long and 6.1 cm wide. | 11.1 cm long and 8.3 cm wide. |
| Mature leaf color, adaxial surface. | Green, RHS NN137A to NN137B, and very narrowly margined yellow-green, RHS 150D. | Green to yellow-green, in between RHS 139A and 147A but darker. |

That which is claimed is:

1. A new and distinct variety of *Clusia rosea* plant named 'LICLUS01', substantially as described and illustrated herein.

* * * * *